United States Patent [19]

Maryanoff et al.

[11] Patent Number: 5,223,541
[45] Date of Patent: Jun. 29, 1993

[54] TRAMADOL N-OXIDE MATERIAL, ENANTIOMERS AND COMPOSITIONS THEREOF, AND THEIR USE

[75] Inventors: Cynthia A. Maryanoff, New Hope; Robert B. Raffa, Norristown; Frank J. Villani, Perkasie, all of Pa.

[73] Assignee: McNeilab, Inc., Spring House, Pa.

[21] Appl. No.: 759,259

[22] Filed: Sep. 13, 1991

[51] Int. Cl.$^5$ .................. A61K 31/13; C07C 291/00
[52] U.S. Cl. .................. 514/644; 514/850; 514/867; 564/299
[58] Field of Search .............. 564/299; 514/644, 850, 514/867

[56] References Cited

U.S. PATENT DOCUMENTS 3,652,589  3/1972  Flick et al. .................. 564/304

Primary Examiner—Richard L. Raymond
Assistant Examiner—P. O'Sullivan
Attorney, Agent, or Firm—Ralph R. Palo

[57] ABSTRACT

This invention relates to a tramadol N-oxide material, enantiomers and compositions thereof and their use. The tramadol N-oxide material and compositions thereof are pharmacologically useful in treating pain, diarrhea and tussive conditions. The tramadol N-oxide is also subject to less side-effects as compared to pure opiate based compositions, such as abuse liability, tolerance, constipation and respiratory depression. Furthermore, the tramadol N-oxide material when administered orally exhibits analgesia for a longer duration than an equi-analgesic amount of tramadol.

7 Claims, 2 Drawing Sheets

TRAMADOL N-OXIDE MATERIAL, ENANTIOMERS AND COMPOSITIONS THEREOF, AND THEIR USE

CROSS REFERENCE

This case is related to application Ser. No. 755,923 and application Ser. No. 755,924, filed on the same day as this case.

BACKGROUND OF THE INVENTION

U.S. Pat. No. 3,652,589 discloses a class of analgesic cycloalkanol-substituted phenol esters having a basic amine group in the cycloalkyl ring. The compound (1RS, 2RS)-2-[(dimethylamino)-methyl]-1-(3-methoxyphenyl)cyclohexanol, commonly known as tramadol, is specifically disclosed therein. A series of articles pertaining to the pharmacology, toxicology and clinical studies of tramadol are found in Arzneim. Forsch. (Drug Res.), 28(I), 114 (1978). Driessen et al., Arch. Pharmacol., 341, R104 (1990) disclose that tramadol produces its analgesic effect through a mechanism that is neither fully opioid-like nor non-opioid-like. The Abstracts of the VIth World Congress on Pain, Apr. 1-6 (1990) disclose that tramadol hydrochloride is an orally active pure opioid agonist analgesic. However, clinical experience indicates that tramadol lacks many of the typical side effects of opioid agonists, e.g., respiratory depression (W. Vogel et al., Arzneim. Forsch. (Drug Res.), 28(I), 183 (1978)), constipation (I. Arend et al., Arzneim. Forsch. (Drug Res.), 28(I), 199 (1978)), tolerance (L. Flohe et al., Arzneim. Forsch. (Drug Res.), 28(I), 213 (1978)), and abuse liability (T. Yanagita, Arzneim. Forsch. (Drug Res.), 28(I), 158 (1978)). When given at a dose of 50 mg by rapid I.V. injection, tramadol may, however, produce certain side effects unique to tramadol including hot flashes and sweating. Another disadvantage to the use of tramadol is that it is an immediate acting drug and thus must be taken a number of times over a 24 hour period to sustain analgesia. Despite these disadvantages, tramadol's combination of non-opioid and opioid activity makes tramadol a very unique drug. Tramadol is currently being marketed by Grunenthal GMBH in Germany as an analgesic.

Opioids have for many years been used as analgesics to treat severe pain. They, however, produce undesirable side effects and as a result cannot be given repeatedly or at high doses. The side effect problems are well documented in the literature. See, J. Jaffe in "Goodman and Gilman's, The Pharmacological Basis of Therapeutics", 8th edition; Gilman et al.; Peragamon Press, New York, 1990; Chapter 22; pages 522-573 wherein it is disclosed that morphine and its congeners, e.g., codeine, hydrocodone and oxycodone, are opioid agonist analgesics that exhibit side effects such as respiratory depression, constipation, tolerance and abuse liability.

In the search for other opiate compounds and in the quest to define the metabolism of opiate compounds, derivatives of opioids have been prepared and examined to assess the pharmacological activity of the derivatives. Flick et al., Arzneim, Forsch., 28, 107 (1978), disclose that the only desmethyl tramadol that exhibits analgesia is the O-desmethyl tramadol, and the reference also discloses that the O-desmethyl tramadol is analgesically more effective than tramadol. B. Klentey et al., Arzneim. Forsch., 7, 594 (1957) disclose that the N-oxides of dihydromorphinone, morphinone and dihydrohydroxycodeinone do not exhibit any analgesic effect. The reference does disclose that the N-oxides exhibit anti-tussive effects and do effect a dose-dependent increase in intestinal tonicity and peristalsis; however, they do not affect the normal blood pressure. Furthermore, the reference discloses that the duration of respiratory depression effected by codeine at a concentration of 10 mg/kg and by dihydrooxycodeinone-N-oxide at concentrations of 5 mg/kg, 10 mg/kg, 20 mg/kg and 40 mg/kg is nearly the same.

The prior art, therefore, does not disclose or suggest an N-oxide of a tramadol material or that the N-oxide of a tramadol material would exhibit an analgesic effect or would exhibit a pharmacological effect having a longer duration, e.g., of analgesia, than its corresponding non-N-oxide, e.g., tramadol.

SUMMARY OF THE INVENTION

Accordingly, the present invention is directed to a tramadol N-oxide material having the following formula I:

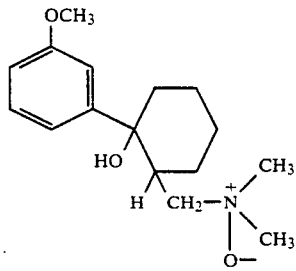

enantiomers and compositions thereof and their use. The tramadol N-oxide material and compositions thereof are pharmacologically useful in treating pain, diarrhea and tussive conditions. The tramadol N-oxide material is also subject to less side-effects as compared to a pure opioid or opiate based compositions, such as abuse liability, tolerance, constipation and respiratory depression. Furthermore, tramadol N-oxide when administered orally exhibits analgesia for a longer duration than an equi-analgesic amount of tramadol. As defined herein longer duration means for more than 2 hours and preferably for 4 to up to at least 5 hours.

BRIEF DESCRIPTION OF THE FIGURES

This invention may be more readily understood by reference to the following figures in which.

DETAILED DESCRIPTION OF THE INVENTION

Figure 1:
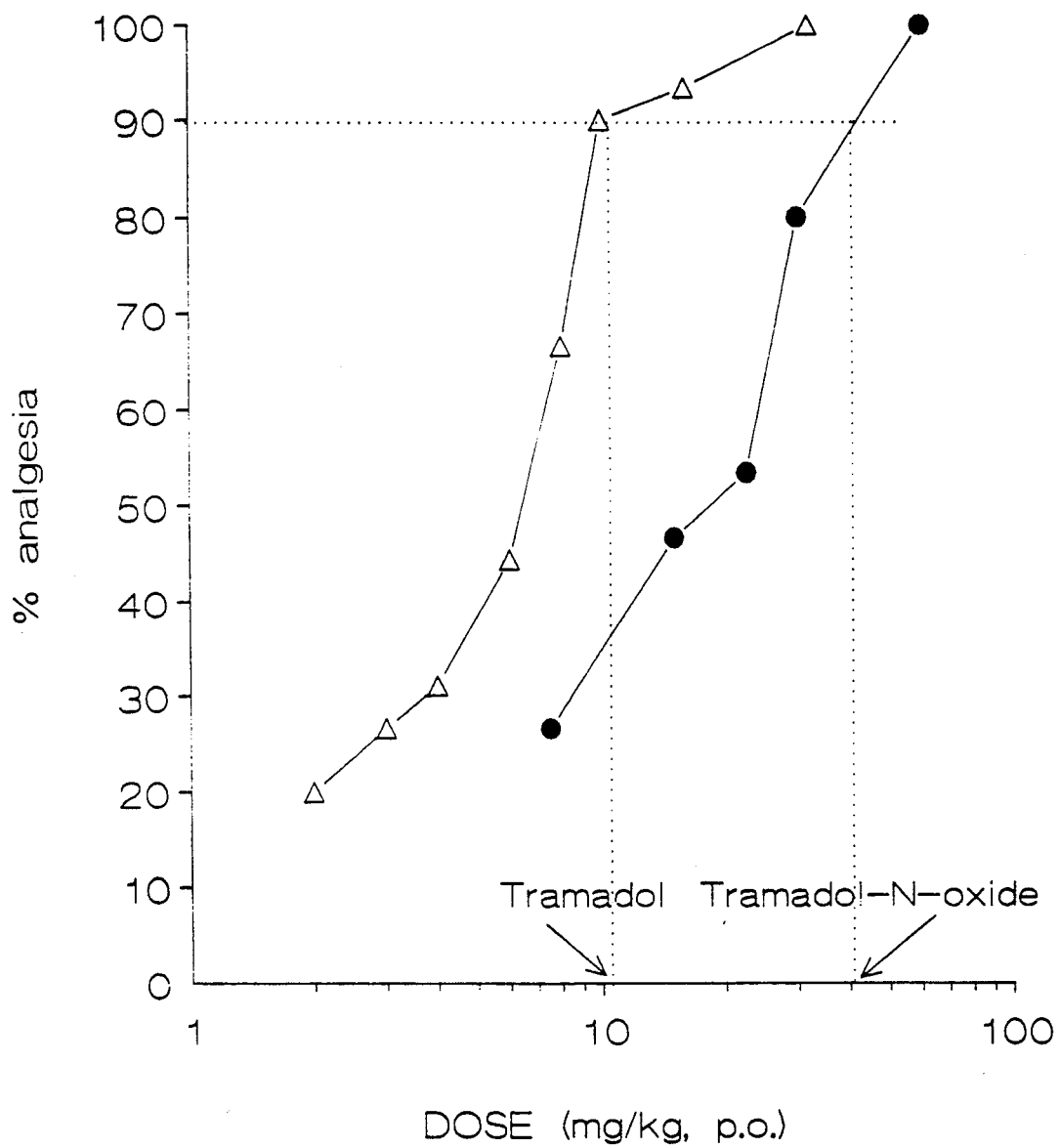
FIG. 1 is a graph showing the % of analgesia effected versus the dose of tramadol and tramadol N-oxide ascertained by the abdominal constriction test in mice.

More particularly, the tramadol N-oxide material according to the present invention is either of the N-oxide derivative of (1R, 2R or 1S, 2S)-2-(dimethylaminomethyl)-1-(3-methoxyphenyl)-cyclohexanol-N-oxide ("tramadol N-oxide") or mixtures thereof. It also includes the individual stereoisomers, such as those of formulas II & III:

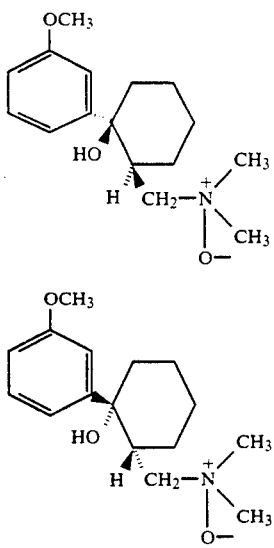

and mixtures of stereoisomers, including racemates. Pharmaceutically acceptable solvates and polymorphs of the compound of formula I are also included.

Tramadol N-oxide is prepared by treating tramadol (commercially available from Grunenthal or may be made by the process described in U.S. Pat. No. 3,652,589, which is herein incorporated by reference) as a free base with an oxidizing agent, such as hydrogen peroxide (30%), in an organic solvent, such as methanol or isopropanol, with and preferably, without heating. See, "Reagents For Organic Synthesis", 1, 471, Fieser & Fieser eds., Wiley N.Y; (1987), B. Kelentey et al., Arzneim. Forsch., 7, 594 (1957). With heating, the reaction takes about 1 hour, whereas without heating the reaction takes about 3 days. Following the oxidation, the mixture is treated with an agent to destroy the excess hydrogen peroxide such as $PtO_2$ or preferably Pt/C, for about a day. The mixture is filtered, followed by the evaporation of the filtrate and then the residue is recrystallized from an organic solvent mixture, e.g., methylene chloride/ethyl acetate. Enantiomeric-N-oxides (formula II, III) are prepared by a similar hydrogen peroxide oxidation of each individual enantiomer.

The tramadol N-oxide material may be used alone or be combined with other active ingredients such as analgesic agents including acetaminophen, codeine, oxycodone, hydrocodone and ibuprofen. This ratio of the tramadol N-oxide material and the other active ingredient will vary depending upon the particular components of the composition.

Pharmaceutical compositions comprising the tramadol N-oxide material alone or in combination with one or more other active ingredients in an intimate admixture with a pharmaceutical carrier can be prepared according to conventional pharmaceutical compounding techniques. The carrier may take a wide variety of forms depending on the form of preparation desired for administration, such as, intravenous, oral or parenteral. The composition may also be administered by means of an aerosol. In preparing the compositions in oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, from about 0.1 to about 25.0 mg/kg, and preferably from about 0.3 to about 12.5 mg/kg of the active ingredients.

The following experimental examples describe the invention in greater particularity and are intended to be a way of illustrating but not limiting the invention.

Example 1: Tramadol N-oxide

Tramadol N-oxide was prepared as set forth hereinafter. Tramadol hydrochloride (0.5 mol) was converted its free base in basified water (pH>9) and then extracted with ether. The solid was then heated under a high vacuum to remove as much water as possible to yield 131.5 g of material. The material was dissolved in methanol (500 mL) and 65 g of 30% $H_2O_2$ was added. The solution was stirred for 3 hours and then an additional 65 g of the 30% $H_2O_2$ was added. The reaction was stirred for 2.5 days at room temperature. Approximately 10 mg of $PtO_2$ (use of Pt/C is suggested for its ease of removal) on carbon was then added to the reaction mixture, and very gentle foaming took place. An additional 10 mg of $PtO_2$ was added and the reaction mixture was stirred overnight and then filtered thru filter aid. The filtrate was concentrated under vacuum while being heated to a temperature <40° C. The residue was taken up in methylene chloride. Since the methylene chloride solution contained some colloidial platinum, the solution was diluted with ethyl acetate to 1 L and filtered through a nylon filter membrane (0.45μ pore size) to yield a clear colorless filtrate. The filtrate was concentrated to 600 mL, and then ethyl acetate was added continuously to maintain a volume of 800 mL while the solution was heated until a vapor temperature of 74° C. was reached. The solution was then cooled to room temperature. The solid was collected by filtration, washed with ethyl acetate and dried in vacuo to yield 126.6 g of the tramadol N-oxide (mp. 159.5°–160° C.).

C16H25N03 Theor.: C, 68.78; H, 9.27; N, 5.01 Found: C, 68.65; H, 9.22; N, 4.99

Example 2: Analgesic Activity

Male CD1 mice (weighing from 18–24 g) were utilized in determining the analgesic effects associated with the compositions of the invention. The mice were all dosed orally with tramadol hydrochloride or tramadol N-oxide (calculated as the base), The procedure used in detecting and comparing the analgesic activity of different classes of analgesic drugs for which there is a good correlation with human efficacy is the prevention of acetylcholine-induced abdominal constriction in mice (H. Collier et al., *Br. J. Pharmacol.*, , 32, 295 (1968)).

Mice, intubated with various doses of tramadol hydrochloride or tramadol N-oxide were injected intraperitoneally with a challenge dose of acetylcholine bromide. The acetylcholine was completely dissolved in distilled water; the abdominal constriction dose 5.5 mg/kg and injected at the rate of 0.20 ml/20 g. For scoring purposes an "abdominal constriction" is defined as a contraction of the abdominal musculature accompanied by arching of the back and extension of the limbs. The mice were observed 10 minutes for the presence or absence of the abdominal constriction response beginning immediately after receiving the acetylcholine dose, which was 30 minutes after receiving the oral administration of tramadol hydrochloride or tramadol N-oxide. Each mouse was used only once.

The percentage of inhibition of the abdominal constriction response (equated to percentage of analgesia) was calculated for each dose as follows:

$$\% \text{ analgesia} = 100 - [(\text{number of responders})/(\text{number per group} \times 100). \quad \{1\}$$

Figure 2:
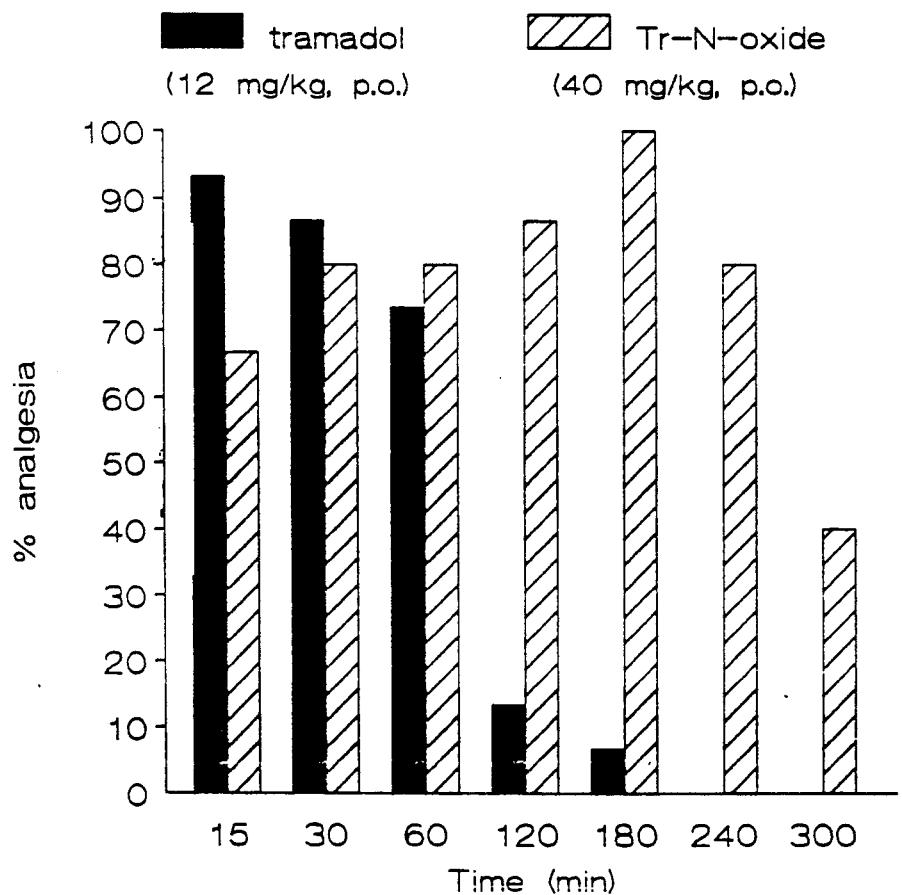
FIG. 2 is a bar graph showing time course of the % of analgesia effected by tramadol N-oxide versus tramadol hydrochloride at equianalgesic doses ascertained by the abdominal constriction test in mice.

For the time-course evaluation studies, an equi-analgesic dose of each compound was first selected based on the dose of each compound which produced an equal level (90%) of analgesia (the ED90 dose). Th ED90 dose of tramadol hydrochloride was estimated to be 12 mg/kg p.o. (See, FIG. 1) and the ED90 dose of tramadol N-oxide was estimated to be 40 mg/kg p.o. (See, FIG. 1). The respective ED90 doses of both compounds were then injected into separate groups of mice at various times prior to the challenge by acetylcholine as described above. Separate groups of mice received either tramadol or tramadol N-oxide at 15, 30, 60, 120, 180, 240 or 300 minutes prior to the acetylcholine challenge. The percentage of analgesia was determined as the percentage of inhibition of the acetylcholine-induced abdominal constriction response according to equation {1}. The duration of analgesic effect (determined as the time percentage analgesia dropped below 50%) of tramadol was between 60 and 120 minutes (See, FIG. 2), whereas the duration of analgesic effect for tramadol N-oxide was between 240 and 300 minutes. The greater duration of analgesic action of tramadol N-oxide at equi-analgesic doses to tramadol also demonstrates that for doses of equal duration, requiring raising the dose of tramadol, the level of tramadol required would be greater than the therpeutically prudent dose and, thus, would likely represent an unacceptable increase in the side effects, and hence, decrease in safety margin of tramadol.

We claim:

1. A compound of the formula I:

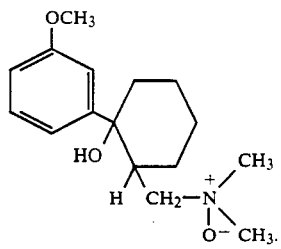

2. An enantiomer of the compound of claim 1 having the formula II:

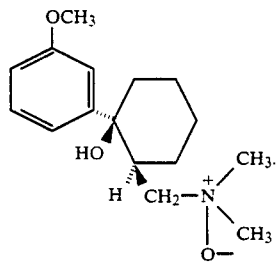

3. An enantiomer of the compound of claim 1 having the formula III:

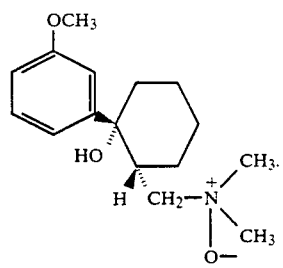

4. A pharmaceutical composition comprising the compound of claim 1 in a therapeutically effective amount and a pharmaceutically acceptable carrier.

5. A method for treating pain, diarrgea, and tussive conditions in a mammal comprising of administrating to the mammal an effective amount for treating the condition of the compound of claim 1.

6. The method of claim 5 wherein the condition is pain.

7. A method of providing a long acting analgesia to a mammal suffering from pain comprising administering to the mammal an effective amount for treating the pain of the compound of claim 1.

* * * * *

UNITED STATES PATENT AND TRADEMARK OFFICE
CERTIFICATE OF CORRECTION

PATENT NO. : 5,223,541
DATED : June 29, 1993
INVENTOR(S) : Cynthia A. Maryanoff, et al.

It is certified that error appears in the above-indentified patent and that said Letters Patent is hereby corrected as shown below:

Col. 6, line 45, change "diarrgea" to "diarrhea".

Signed and Sealed this

Thirtieth Day of August, 1994

Attest:

BRUCE LEHMAN

*Attesting Officer*          *Commissioner of Patents and Trademarks*